(12) United States Patent
Boardman et al.

(10) Patent No.: US 6,824,882 B2
(45) Date of Patent: Nov. 30, 2004

(54) FLUORINATED PHOSPHONIC ACIDS

(75) Inventors: Larry D. Boardman, Woodbury, MN (US); Mark J. Pellerite, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 9 days.

(21) Appl. No.: 10/161,258

(22) Filed: May 31, 2002

(65) Prior Publication Data

US 2003/0228469 A1 Dec. 11, 2003

(51) Int. Cl.$^7$ .......................... B32B 15/04; C01B 25/10; C07F 9/42
(52) U.S. Cl. .................... 428/457; 428/469; 428/472.3; 423/301; 562/8; 562/26
(58) Field of Search .............................. 428/469, 472.3, 428/457; 562/8, 25; 423/301

(56) References Cited

U.S. PATENT DOCUMENTS

| | | |
|---|---|---|
| 3,145,222 A | 8/1964 | Brace |
| 3,937,724 A | 2/1976 | Chance et al. |
| 4,094,911 A | 6/1978 | Mitsch et al. |
| 4,145,382 A | 3/1979 | Hayashi et al. |
| 4,736,051 A | 4/1988 | Wakatsuki et al. |
| 5,011,963 A | 4/1991 | Ogawa et al. |
| 5,023,279 A | * 6/1991 | Buckmaster et al. .......... 521/85 |
| 5,162,292 A | * 11/1992 | Evans et al. ................ 503/227 |

(List continued on next page.)

FOREIGN PATENT DOCUMENTS

| | | |
|---|---|---|
| EP | 0 606 640 A1 | 7/1994 |
| FR | 2 616 150 | 12/1988 |
| JP | 60-144377 | 7/1985 |
| JP | 08198975 A | 8/1996 |
| JP | 08199034 | 8/1996 |
| JP | 2002-60979 | 2/2002 |
| WO | WO 99/37626 | 7/1999 |
| WO | WO 00/29639 | 5/2000 |
| WO | WO 00/66667 | 11/2000 |
| WO | WO 01/30873 A1 | 5/2001 |
| WO | WO 02/24792 A2 | 3/2002 |

OTHER PUBLICATIONS

Rong et al., "The Addition of Perfluorobutyl Iodide to Carbon–Carbon Multiple Bonds and the Preparation of Perfluorobutylalkenes", Tetrahedron Letters, vol. 31, No. 39, pp. 5615–5616, 1990.

Zhou et al., "A Convenient Synthesis of 2–Alkyl–3–Fluoro–3–Polyfluoroalkyl–2–Propenals", Journal of Fluorine Chemistry, vol. 39, pp. 323–327, 1988.

Naud et al., "Critical Influence of the Fluorinated Chain Length in the Self–Assembly of Terminally Perfluorinated Alkanethiol Monolayers on Gold Surfaces. An Electrochemical Study", Langmuir, vol. 17, pp. 4851–4857, 2001.

Bhattacharya et al., "The Michaelis–Arbuzov Rearrangement", Chem. Rev., vol. 81, pp. 415–430, 1981.

Fukushima et al., "Microstructure, Wettability, and Thermal Stability of Semifluorinated Self–Assembled Monolayers (SAMs) on Gold", J. Phys. Chem. B., vol. 104, pp. 7417–7423, 2000.

Mirviss, "Synthesis of ω–Unsaturated Acids", J. Org. Chem., vol. 54, pp. 1948–1951, 1989.

Brace, "Synthesis with perfluoroalkyl radicals from perfluoroalkyl idodides. A rapid survey of synthetic possibilities with emphasis on practical applications. Part one: alkenes, alkynes and allylic compounds", Elsevier, Journal of Fluorine Chemistry, vol. 93, pp. 1–25, 1999.

Yang et al., "Growth and Characterization of Metal (II) Alkanebisphosphonate Multilayer Thin Films on Gold Surfaces", J. Am. Chem. Soc., 1993, 115, pp. 11855–11862.

Van Alsten, John G., "Self–Assembled Monolayers on Engineering Metals: Structure, Derivatization, and Utility", Langmuir, 1999, 15, pp. 7605–7614.

Folkers et al., "Self Assembled Monolayers of Long–Chain Hyrdomaxic Acids on the Native Oxides of Metals", Langmuir, 1995, 11, pp. 813–824.

Jeanmarie et al., "Synthese De Nouveaux Derives Phosphones a Chaine Perfluoree et Leurs Proprietes Adhesives Sur Acier", Phosphorus, Sulfur and Silicon, vol. 177, No. 10, pp. 2331–2343 (2002).

Brodino et al., "Synthesis of New Phosphonic Derivatives with Fluorinated Chains", Journal of Fluorine Chemistry, vol. 76, No. 2, pp. 193–200 (1996).

Primary Examiner—Monique R. Jackson
(74) Attorney, Agent, or Firm—Bradford B. Wright

(57) ABSTRACT

Fluorinated phosphonic acid compounds, useful as treatments for substrate surfaces, have the formula:

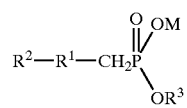

wherein:

$R^1$ is a straight chain alkylene group having from about 3 to about 21 carbon atoms, an oxa-substituted straight chain alkylene group having from about 2 to about 20 carbon atoms, or a thia-substituted straight chain alkylene group having from about 2 to about 20 carbon atoms;

$R^2$ is a perfluoroalkyl group having from about 4 to about 10 carbon atoms;

$R^3$ is hydrogen, an alkali metal cation, or an alkyl group having from about 1 to about 6 carbon atoms; and M is hydrogen or an alkali metal cation, with the proviso that if $R^1$ is an unsubstituted straight chain alkylene group, then the sum of carbon atoms in $R^1$ and $R^2$ combined is at least 10.

22 Claims, No Drawings

U.S. PATENT DOCUMENTS

| | | |
|---|---|---|
| 5,178,916 A | 1/1993 | Chidsey et al. |
| 5,219,654 A | 6/1993 | Singh et al. |
| 5,266,650 A | 11/1993 | Guerra et al. |
| 5,277,788 A | 1/1994 | Nitowski et al. |
| 5,384,374 A | 1/1995 | Guerra et al. |
| 5,766,698 A | 6/1998 | Singh et al. |
| 5,807,913 A | 9/1998 | Mikuni et al. |
| 5,851,674 A | 12/1998 | Pellerite et al. |
| 6,063,730 A * | 5/2000 | Simpson et al. ............ 503/227 |
| 6,210,840 B1 | 4/2001 | Usami et al. |
| 6,277,485 B1 | 8/2001 | Invie et al. |
| 6,380,101 B1 * | 4/2002 | Breen et al. ................ 438/765 |
| 6,486,245 B1 * | 11/2002 | Thunemann et al. ....... 524/130 |

* cited by examiner

FLUORINATED PHOSPHONIC ACIDS

TECHNICAL FIELD

The present invention relates to fluorinated organic compounds that self-assemble to form monolayers, and in particular to fluorinated phosphonic acids.

BACKGROUND

Self-assembling materials, as their name implies, spontaneously form a structure (e.g., micelle or monolayer) when they contact another substance. Monolayer formation is particularly useful when it occurs on the surface of a solid substrate (e.g., a piece of metal). If a monolayer is formed from a material that imparts a low surface energy to a surface of a substrate, then one or more useful properties such as water repellency, corrosion resistance, lubricity, and adhesive release may be imparted to that surface. If the surface energy is low enough, oil repellency and soil (i.e., stain) resistance may be achieved. Generally, surface energies this low may be achieved through use of fluorocarbon materials.

Fluorinated self-assembled monolayers have been employed in soil resistant coatings, anti-reflective glass coatings, and release coatings. Typical self-assembling materials consist of a polar head group attached to a hydrophobic tail. Despite their relatively higher cost, self-assembling materials having a fluorinated tail have gained wide acceptance in industry. This is because they typically substantially outperform alternative materials, such as those having a hydrocarbon or silicone tail, for example, in terms of adhesive release and soil resistance. Commercial products in this area have typically utilized materials bearing seven- and eight-carbon perfluoroalkyl groups. Recently, there has been a significant effort in industry to find alternative materials to such groups.

It would be desirable to have new materials that self-assemble to form monolayers having low surface energies on a wide range of substrates, and it would be especially desirable that such materials not contain seven- and eight-carbon perfluoroalkyl groups.

SUMMARY OF THE PRESENT INVENTION

In one aspect, the present invention provides a fluorinated phosphonic acid compound having the formula:

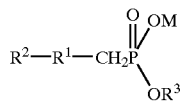

wherein:
- $R^1$ is a straight chain alkylene group having from about 3 to about 21 carbon atoms, an oxa-substituted straight chain alkylene group having from about 2 to about 20 carbon atoms, or a thia-substituted straight chain alkylene group having from about 2 to about 20 carbon atoms;
- $R^2$ is a perfluoroalkyl group having from about 4 to about 10 carbon atoms;
- $R^3$ is hydrogen, an alkali metal cation, or an alkyl group having from about 1 to about 6 carbon atoms; and
- M is hydrogen or an alkali metal cation, with the proviso that if $R^1$ is an unsubstituted straight chain alkylene group, then the sum of carbon atoms in $R^1$ and $R^2$ combined is at least 10.

In another aspect, the present invention provides a method of treating the surface of an article, the method comprising:
- providing a substrate having a surface; and
- applying a fluorinated phosphonic acid compound to the surface of the substrate, the compound having the formula:

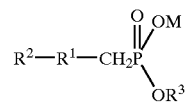

wherein:
- $R^1$ is a straight chain alkylene group having from about 3 to about 21 carbon atoms, an oxa-substituted straight chain alkylene group having from about 2 to about 20 carbon atoms, or a thia-substituted straight chain alkylene group having from about 2 to about 20 carbon atoms;
- $R^2$ is a perfluoroalkyl group having from about 4 to about 10 carbon atoms;
- $R^3$ is hydrogen, an alkali metal cation, or an alkyl group having from about 1 to about 6 carbon atoms; and
- M is hydrogen or an alkali metal cation, with the proviso that if $R^1$ is an unsubstituted straight chain alkylene group, then the sum of carbon atoms in $R^1$ and $R^2$ combined is at least 10.

In another aspect, the present invention provides an article comprising a substrate having a surface, the surface intimately contacting at least a partial monolayer of a fluorinated phosphonic acid compound having the formula:

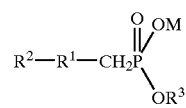

wherein:
- $R^1$ is a straight chain alkylene group having from about 3 to about 21 carbon atoms, an oxa-substituted straight chain alkylene group having from about 2 to about 20 carbon atoms, or a thia-substituted straight chain alkylene group having from about 2 to about 20 carbon atoms;
- $R^2$ is a perfluoroalkyl group having from about 4 to about 10 carbon atoms;
- $R^3$ is hydrogen, an alkali metal cation, or an alkyl group having from about 1 to about 6 carbon atoms; and
- M is hydrogen or an alkali metal cation, with the proviso that if $R^1$ is an unsubstituted straight chain alkylene group, then the sum of carbon atoms in $R^1$ and $R^2$ combined is at least 10.

In another aspect, the present invention provides an article prepared by a process, the process comprising:
- providing a substrate having a surface; and
- applying a fluorinated phosphonic acid compound to the surface of the substrate, the compound having the formula:

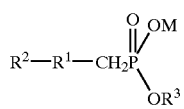

wherein:

$R^1$ is a straight chain alkylene group having from about 3 to about 21 carbon atoms, an oxa-substituted straight chain alkylene group having from about 2 to about 20 carbon atoms, or a thia-substituted straight chain alkylene group having from about 2 to about 20 carbon atoms;

$R^2$ is a perfluoroalkyl group having from about 4 to about 10 carbon atoms;

$R^3$ is hydrogen, an alkali metal cation, or an alkyl group having from about 1 to about 6 carbon atoms; and M is hydrogen or an alkali metal cation, with the proviso that if $R^1$ is an unsubstituted straight chain alkylene group, then the sum of carbon atoms in $R^1$ and $R^2$ combined is at least 10.

Fluorinated phosphonic acids of the present invention self-assemble (e.g., forming monolayer films) when applied to a wide variety of substrates, resulting in coatings on the substrates that exhibit at least one of low surface energy, adhesive release, lubricity, water repellency, and/or soil resistance.

As used herein:

"perfluoro" refers to the exhaustive substitution of hydrogen by fluorine in the group or molecule to which it refers.

DETAILED DESCRIPTION

Fluorinated phosphonic acids of the present invention have the formula

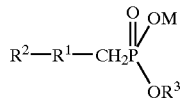

wherein:

$R^1$ is a straight chain alkylene group having from about 3 to about 21 carbon atoms, an oxa-substituted straight chain alkylene group having from about 2 to about 20 carbon atoms, or a thia-substituted straight chain alkylene group having from about 2 to about 20 carbon atoms. Desirably, $R^1$ is a straight chain alkylene group having from about 5 to about 21 carbon atoms, more desirably $R^1$ is a straight chain alkylene group having from about 10 to about 21 carbon atoms. Two useful straight chain alkylene groups are decane-1,10-diyl and heneicosane-1,21-diyl. Without wishing to be bound by theory, it is believed that oxygen atoms and/or sulfur atoms, being of similar steric size to methylene (i.e., —$CH_2$—), may be substituted for methylene groups of the alkylene chain without significantly disrupting the self-assembling nature and/or performance characteristics of fluorinated phosphonic acids according to the present invention. Thus, oxa-or thia-substitution (i.e., replacement of a methylene by an O or S atom) may occur at a single site, or at multiple sites, along the alkylene chain without adverse affect, and are encompassed by the present invention.

$R^2$ is a perfluoroalkyl group having from about 4 to about 10 carbon atoms with the proviso that if $R^1$ is an unsubstituted straight chain alkylene group, then the sum of carbon atoms in $R^1$ and $R^2$ combined is at least 10. Exemplary perfluoroalkyl groups include isomers of perfluorobutyl, perfluoropentyl, perfluorohexyl, and mixtures thereof. Desirably, $R^2$ is a perfluoro-n-butyl group.

$R^3$ is hydrogen, an alkali metal cation (e.g., lithium, sodium, potassium), or an alkyl group having from about 1 to about 6 carbon atoms (e.g., methyl, ethyl, butyl, hexyl). Desirably, $R^3$ is hydrogen or an alkali metal.

M is hydrogen or an alkali metal cation.

Although there is wide latitude in the choice of $R^1$ and $R^2$, it is desirable that the total chain length be sufficiently long that desirable properties are obtained. Thus, it is desirable that the sum of carbon atoms in $R^1$ and $R^2$ combined is at least 10.

Fluorinated phosphonic acids of the present invention can be prepared by a variety of well known procedures (e.g., by a Michaelis-Arbuzov reaction on the corresponding alkyl chlorides, bromides, or iodides followed by hydrolysis, as described, for example, by Bhatacharya et al. in Chemical Reviews (1981), vol. 81, pp. 415–430, the disclosure of which is incorporated herein by reference; or by addition of a perfluoroalkyl iodide to an olefin having the structure $CH_2=CH(CH_2)_m PO_3 H_2$, or an ester thereof, followed by reduction according to the general method of Rong et al. in Tetrahedron Letters (1990), vol. 31, pp. 5615–5616, the disclosure of which is incorporated herein by reference).

Fluorinated phosphonic acids of the present invention may be advantageously applied to a wide variety of substrates, whereby they may form a monolayer covering at least a portion of surface of the substrate. Such a monolayer is typically oriented such that the phosphono group contacts the substrate surface with the perfluoroalkyl group extending away from the substrate surface. Fluorinated phosphonic acids of the present invention may be advantageously applied to the native oxide surface layer of a variety of metallic substrates, although other substrates are also useful. Exemplary metals include chromium, aluminum, copper, nickel, titanium, silver, and alloys and mixtures thereof. Exemplary other materials include metal oxides and mixed metal oxides and nitrides including alumina, titania, titanium nitride, and indium tin oxide. Desirably, the substrate comprises chromium, aluminum, copper, and/or nickel.

Exemplary methods for applying the fluorinated phosphonic acids of the present invention to a substrate include, for example, spraying, dip coating, wiping, and spin coating of a dilute (e.g., an 0.1 weight percent) solution of the acid in an organic solvent such as ethanol or isopropyl alcohol. Depending on exact coating conditions used, some of these methods may apply an amount of fluorinated phosphonic acid in excess of one monolayer. In such cases, the excess material is at most only weakly bound and typically can be removed easily by rinsing with an appropriate solvent. Typically, fluorinated phosphonic acids of the present invention are applied as a layer to at least a portion, desirably all, of the substrate surface to be treated. Desirably, the fluorinated phosphonic acid forms a monolayer (e.g., a self-assembled monolayer) on the surface of the substrate. The layer of fluorinated phosphonic acid may be of any thickness, but after rinsing away any excess unbound material and drying, the thickness is typically in the range of from about 0.5 to about 10 nanometers (nm), desirably in the range of from about 1 to about 5 nm, more desirably in the range of from about 1 to about 2.5 nm.

Fluorinated phosphonic acids of the present invention have applicability, for example, as mold release agents, soil resistant coatings, lubricity coatings, water-repellent coatings, and/or in fabrication of microfluidic and/or microelectromechanical devices.

Objects and advantages of this invention are further illustrated by the following examples, but the particular materials and amounts thereof recited in these examples, as well as other conditions and details should not be construed to unduly limit this invention.

EXAMPLES

All parts, percentages and ratios in the following preparations and examples are by weight unless stated otherwise.

1-Iodo-1H,1H,2H,2H-perfluorodecane and 1-iodo-1H,1H,2H,2H-perfluorohexane were obtained from Lancaster Synthesis, Windham, N.H.

7-Octen-1-ol was obtained from TCI America, Portland, Oreg.

21-Docosenoic acid was prepared as described by Mirviss, S. B. in The Journal of Organic Chemistry (1989), vol. 54, pp. 1948–1951.

"Room temperature" in the following preparations and examples means approximately 20° C.–24° C.

"Overnight" in the following preparations and examples means approximately 14–16 hours (hr).

"Nonafluorobutyl" in the following preparations refers to the linear isomeric structure $-CF_2CF_2CF_2CF_3$.

Unless otherwise noted, all reagents used in the following preparations and examples were obtained, or are available, from general chemical suppliers such as Aldrich Chemical Co., Milwaukee, Wis., or may be synthesized by known methods.

Preparation of $CF_3(CF_2)_7CH_2CH_2PO_3H_2$

A mixture of 42.8 grams (g) of 1-iodo-1H,1H,2H,2H-perfluorodecane and 37.4 g of triethyl phosphite was heated for 40 hr at 150° C. Diethyl ethylphosphonate and other volatiles were removed from the mixture by distillation, b.p. 30–50° C. at 0.05 torr (7 Pa). Distillation of the remaining concentrated mixture provided 23.1 g of a 73:16:11 mixture of 1-(diethylphosphono)-1H,1H,2H,2H-perfluorodecane, ethyl 1H,1H,2H,2H-perfluorodecyl ethylphosphonate, and ethyl ethylphosphonate, b.p. 102–109° C. at 0.05 torr (7 Pa).

To a solution of 17.5 g of the above mixture in 100 mL of dichloromethane was added 10.7 g of bromotrimethylsilane. After 24 hr at room temperature, the solution was concentrated to a pale yellowish liquid, and the intermediate silylphosphonate ester was dissolved in 200 mL of methanol. The resultant solution was stirred at room temperature for 30 minutes (min), and then concentrated to give an off-white solid. Dissolution in methanol and concentration, as above, were repeated two more times. The crude product mixture was triturated with water, and recrystallization of 7.3 g of material from ethyl acetate gave 3.1 g of 1-phosphono-1H,1H,2H,2H-perfluorodecane $(CF_3(CF_2)_7CH_2CH_2PO_3H_2)$ as white crystals, m.p. 170–178° C.

Preparation of $CF_3(CF_2)_3CH_2CH_2PO_3H_2$

A mixture of 37.4 g of 1-iodo-1H,1H,2H,2H-perfluorohexane and 50.0 g of triethyl phosphite was heated at 150° C. After 16 hr, an additional 50.0 g of triethyl phosphite was added, and heating was continued. After 2 hr, an additional 50.0 g of triethyl phosphite was again added, and heating was continued for another 24 hr. Diethyl ethylphosphonate and other volatiles were removed by distillation through a 12-inch (30 cm) vacuum-jacketed packed column, b.p. 34–38° C. at 0.05 torr (7 Pa). Distillation of the concentrate provided 22.3 g of 1-diethylphosphono-1H,1H,2H,2H-perfluorohexane as a 90:2:7 mixture with triethyl phosphate and ethyl 1H,1H,2H,2H-perfluorohexyl ethylphosphonate as a clear, colorless liquid, b.p. 47–51° C. at 0.05 torr (7 Pa).

To a solution of 15.37 g of the above mixture in 100 mL of dichloromethane was added 15.31 g of bromotrimethylsilane. After 24 hr at room temperature, the solution was concentrated to a light yellowish liquid, and the intermediate silylphosphonate ester was dissolved in 200 mL of methanol. The resultant solution was stirred at room temperature for 30 min and concentrated to a white solid. Dissolution in methanol and concentration were repeated two times, and the crude product was recrystallized from acetonitrile to yield 8.89 g of 1-phosphono-1H,1H,2H,2H-perfluorohexane $(CF_3(CF_2)_3CH_2CH_2PO_3H_2)$ as colorless plates, m.p. 160–162° C.

Preparation of $CF_3(CF_2)_3(CH_2)_6PO_3H_2$

To a solution of 187.4 g of perfluorobutyl iodide and 100.2 g of 5-hexen-1-ol in a mixture of 1.4 liters of acetonitrile and 0.6 liter of water, was added a mixture of 100.8 g of sodium bicarbonate and 200.2 g of sodium dithionite in portions with stirring. The reaction mixture was stirred at room temperature overnight and acidified with 1 N hydrochloric acid. The mixture was extracted with diethyl ether, and the combined organic phases were washed with saturated aqueous sodium bicarbonate, then with brine, and then dried over anhydrous magnesium sulfate. The solution was concentrated, and $^1H$ NMR analysis (i.e., $^1H$ nuclear magnetic resonance spectroscopy) of the concentrate indicated an approximately 3:1 mixture of 5-hexen-1-ol and 5-iodo-6-(nonafluorobutyl)-1-hexanol. The concentrate was combined with 100 mL of ethyl acetate, 100.0 g of perfluorobutyl iodide, and 0.82 g of 2,2'-azobisisobutyronitrile, and the resultant solution was degassed and heated at 70° C. After 24 hr, $^1H$ NMR analysis of a concentrated aliquot indicated an approximately 2:1 mixture of 5-hexen-1-ol and 5-iodo-6-(nonafluorobutyl)-1-hexanol. An additional 50.0 g of perfluorobutyl iodide and 0.82 g of 2,2'-azobisisobutyronitrile were added, and heating at 70° C. was continued for 24 hr. Concentration of the mixture afforded 146.1 g of crude 5-iodo-6-(nonafluorobutyl)-1-hexanol as an approximately 8:1 mixture with 5-hexen-1-ol as an orange liquid. The crude product was used without further purification.

To a slurry of 165.0 g of zinc powder in 1 liter of ethanol was added 10.0 g of acetic acid. A solution of the crude product mixture above in 100 mL of ethanol was added dropwise with stirring over 1 hr, and the reaction mixture was heated at 50° C. for 4 hr. The mixture was filtered, and the filtrate was concentrated. The concentrate was dissolved in chloroform, and the solution was filtered and concentrated to 149.0 g of a viscous, light yellow liquid. Bulb-to-bulb distillation of a 65.0 g portion of the concentrate afforded 18.1 g of 6-(nonafluorobutyl)-1-hexanol as a slightly yellowish liquid, b.p. 130–140° C. at 0.05 torr (7 Pa).

To a mixture of 18.00 g of 6-(nonafluorobutyl)-1-hexanol and 225 mL of 48 weight percent hydrobromic acid was slowly added 23 mL of concentrated sulfuric acid. The reaction mixture was heated at 100° C. for 12 hr and poured into 1 liter of water. The mixture was extracted with hexanes, and the combined organic phases were then washed with saturated aqueous sodium bicarbonate and dried over anhydrous magnesium sulfate. The hexanes solution was concentrated to a light amber liquid, which was eluted through 2 inches (5 cm) of silica with hexanes. Concentration of the eluent yielded a light amber liquid, and bulb-to-bulb distillation gave 18.29 g of 1-bromo-6-(nonafluorobutyl)hexane as a clear, colorless liquid, b.p. 70–80° C. at 0.05 torr (7 Pa).

A mixture of 18.04 g of 1-bromo-6-(nonafluorobutyl)hexane and 19.6 g of triethyl phosphite was heated at 150° C. After 18 hr, an additional 10.0 g of triethyl phosphite was added, and heating was continued for 8 hr more. Diethyl ethylphosphonate and other volatiles were removed by distillation, b.p. 30–50° C. at 0.05 torr (7 Pa), and bulb-to-bulb distillation of the concentrate provided 18.88 g of 1-(diethylphosphono)-6-(nonafluorobutyl)hexane as a clear, colorless liquid, b.p. 120–130° C. at 0.05 torr (7 Pa).

To a solution of 18.63 g of 1-(diethylphosphono)-6-(nonafluorobutyl)hexane in 100 mL of dichloromethane was added 16.8 g of bromotrimethylsilane. After 18 hr at room temperature, the solution was concentrated to a nearly colorless liquid, and the intermediate silylphosphonate ester was dissolved in 250 mL of methanol. The resultant solution was stirred at room temperature for 30 min and concentrated to a white solid. Dissolution in methanol and concentration were repeated two times, and two recrystallizations of the crude product from a 99:1 mixture of heptane and 2-propanol gave 12.50 g of 1-phosphono-6-(nonafluorobutyl)hexane ($CF_3(CF_2)_3(CH_2)_6PO_3H_2$) as colorless leaves, m.p. 107–108° C.

Preparation of $CF_3(CF_2)_3(CH_2)_4PO_3H_2$

To a solution of 190.3 g of perfluorobutyl iodide and 36.1 g of 3-buten-1-ol in a mixture of 560 mL of acetonitrile and 240 mL of water was added, in portions with stirring, a mixture of 48.3 g of sodium bicarbonate and 95.8 g of sodium dithionite. The reaction mixture was stirred at room temperature overnight and acidified with 1 N hydrochloric acid. The mixture was extracted with diethyl ether, and the combined organic phases were washed with saturated aqueous sodium bicarbonate, then with brine, and then dried over anhydrous magnesium sulfate. Concentration provided 38.5 g of an orange liquid, which was dissolved in 50 mL of ethanol. This solution was added to a stirred slurry of 29.42 g of zinc powder in 400 mL of ethanol and heated at 50° C. for 4 hr and filtered, and the filtrate was concentrated to 39.15 g of a clear, light orange liquid. Bulb-to-bulb distillation of a 10.0 g portion of this material afforded 5.20 g of 4-(nonafluorobutyl)-1-butanol as a clear, colorless liquid, b.p. 105–115° C. at 0.10 torr (14 Pa).

To a mixture of 12.50 g of 4-(nonafluorobutyl)-1-butanol and 150 mL of 48 weight percent hydrobromic acid was slowly added 15 mL of concentrated sulfuric acid. The reaction mixture was heated at 100° C. for 18 hr, and then poured into 500 mL of water. The mixture was extracted with hexanes, and the combined organic phases were washed with saturated aqueous sodium bicarbonate and dried over anhydrous magnesium sulfate. Filtration and concentration afforded 12.50 g of crude 1-bromo-4-(nonafluorobutyl)butane as a light amber liquid, which was used without further purification.

A mixture of 12.40 g of 1-bromo-4-(nonafluorobutyl)butane and 21.00 g of triethyl phosphite was heated at 150° C. After 18 hr, diethyl ethylphosphonate and other volatiles were removed from the mixture by distillation, b.p. 30–50° C. at 0.05 torr (7 Pa). Bulb-to-bulb distillation of the remaining concentrated mixture provided 13.0 g of 1-(diethylphosphono)-4-(nonafluorobutyl)butane as a clear, colorless liquid, b.p. 105–110° C. at 0.05 torr (7 Pa).

To a solution of 11.54 g of 1-(diethylphosphono)-4-(nonafluorobutyl)butane in 50 mL of dichloromethane was added 10.7 g of bromotrimethylsilane. After 18 hr at room temperature, the solution was concentrated to a nearly colorless liquid, and the intermediate silylphosphonate ester was dissolved in 250 mL of methanol. The resultant solution was stirred at room temperature for 1 hr, and then concentrated to give a white solid. Dissolution in methanol and concentration were repeated two more times, and recrystallization of the crude product from acetonitrile gave 8.39 g of 1-phosphono-4-(nonafluorobutyl)butane ($CF_3(CF_2)_3(CH_2)_4PO_3H_2$) as colorless needles, m.p. 123–124° C.

Example 1

This example describes the preparation of $CF_3(CF_2)_3(CH_2)_8PO_3H_2$.

To a solution of 190.70 g of perfluorobutyl iodide and 38.47 g of 7-octen-1-ol in a mixture of 480 mL of acetonitrile and 180 mL of water was added a mixture of 29.40 g of sodium bicarbonate and 58.33 g of sodium dithionite in portions with stirring. The reaction mixture was stirred at room temperature overnight and acidified with 1 N hydrochloric acid. The mixture was diluted with 400 mL of water and extracted with 3×200 mL portions of diethyl ether, and the combined organic phases were washed with 2×200 mL portions of saturated aqueous sodium bicarbonate and one 200 mL portion of brine and dried over anhydrous magnesium sulfate. Concentration afforded crude 7-iodo-8-(nonafluorobutyl)-1-octanol as a light yellow liquid, which was used without further purification.

To a slurry of 98.0 g of zinc powder in 600 mL of ethanol was added 3.0 g of acetic acid. A solution of the crude 7-iodo-8-(nonafluorobutyl)-1-octanol prepared above in 100 mL of ethanol was added dropwise with stirring over 15 min, and the reaction mixture was heated at 50° C. for 3 hr. The mixture was filtered, and the filtrate was concentrated to 100.0 g of a viscous, light yellow fluid. A 79.6 g portion of this material was stirred with 300 mL of hexanes, and the supernatant was filtered through diatomaceous earth (marketed under the trade designation "CELITE" by Johns-Manville Corporation, Denver, Colo.) and concentrated to give 44.24 g of 8-(nonafluorobutyl)-1-octanol as a clear, colorless oil, which was used without further purification.

To a mixture of 15.22 g of 8-(nonafluorobutyl)-1-octanol and 200 mL of 48 weight percent hydrobromic acid was slowly added 20 mL of concentrated sulfuric acid. The reaction mixture was heated at 100° C. for 18 hr and poured into 800 mL of water. The mixture was extracted with 2×200 mL portions of hexanes, and the combined organic phases were washed with 2×200 mL portions of saturated aqueous sodium bicarbonate, 2×200 mL portions of 3 formal aqueous sodium thiosulfate, and one 100 mL portion of brine, and then dried over anhydrous magnesium sulfate. The solution was concentrated to a dark liquid, which was eluted through 2 inches (5 cm) of silica with 500 mL of hexanes. Concentration of the eluent yielded a clear, light yellow liquid, and bulb-to-bulb distillation gave 9.14 g of 1-bromo-8-(nonafluorobutyl)octane as a clear, light yellow liquid, b.p. 105–110° C. at 0.05 torr (7 Pa).

A mixture of 8.24 g of 1-bromo-8-(nonafluorobutyl)octane and 8.31 g of triethyl phosphite was heated at 150° C. After 15 hr an additional 4.30 g of triethyl phosphite was added, and heating was continued for 4 hr. Diethyl ethylphosphonate and other volatiles were removed by distillation, b.p. 30–50° C. at 0.05 torr (7 Pa). Bulb-to-bulb distillation of the concentrate provided 8.72 g of 1-(diethylphosphono)-8-(nonafluorobutyl)octane as a clear, colorless liquid, b.p. 115–125° C. at 0.08 torr (11 Pa).

To a solution of 7.03 g of 1-(diethylphosphono)-8-(nonafluorobutyl)octane in 30 mL of dichloromethane was added 6.12 g of bromotrimethylsilane. After 18 hr at room temperature, the solution was concentrated to a pale yellow liquid, and the intermediate silylphosphonate ester was dissolved in 150 mL of methanol. The resultant solution was stirred at room temperature for 30 min and concentrated to a white solid. Dissolution in methanol and concentration were repeated two times, and two recrystallizations of the crude product from acetonitrile gave 4.68 g of 1-phosphono-8-(nonafluorobutyl)octane $(CF_3(CF_2)_3(CH_2)_8PO_3H_2)$ as white crystals, m.p. 87–89° C.

Example 2

The example describes the preparation of $CF_3(CF_2)_3(CH_2)_{11}PO_3H_2$.

To a solution of 199.7 g of perfluorobutyl iodide and 93.7 g of 10-undecen-1-ol in a mixture of 700 mL of acetonitrile and 300 mL of water, was added a mixture of 53.8 g of sodium bicarbonate and 106.2 g of sodium dithionite in small portions with stirring. The reaction mixture was stirred at room temperature overnight and acidified with 1N hydrochloric acid. The mixture was extracted with diethyl ether, and the combined organic phases were sequentially washed with saturated aqueous sodium bicarbonate and brine, and then dried over anhydrous magnesium sulfate. Concentration of the ether solution afforded 234.4 g of crude 10-iodo-11-(nonafluorobutyl)-1-undecanol as a viscous, light amber liquid, which was used without further purification.

To a slurry of 130.0 g of zinc powder in 500 mL of ethanol was added 5.0 g of acetic acid. A solution of 230.0 g of the crude 10-iodo-11-(nonafluorobutyl)-1-undecanol prepared above in 100 mL of ethanol was added dropwise with stirring over 1 hr. Then, the reaction mixture was heated at 50° C. for 4 hr. The mixture was filtered, and the filtrate was concentrated to a viscous, light yellow liquid. Bulb-to-bulb distillation of the liquid, in several portions, provided 97.3 g of 11-(nonafluorobutyl)-1-undecanol as a colorless solid, b.p. 160–200° C. at 0.05 torr (7 Pa).

To a mixture of 19.52 g of 11-(nonafluorobutyl)-1-undecanol and 200 mL of 48 weight percent hydrobromic acid was slowly added 20 mL of concentrated sulfuric acid. The reaction mixture was heated at 100° C. for 24 hr and poured into 1 liter of water. The mixture was extracted with hexanes, and the combined organic phases were washed with saturated aqueous sodium bicarbonate and dried over anhydrous magnesium sulfate. The solution was concentrated to an amber liquid, which was eluted through 3 inches of silica with hexanes. Concentration of the eluent yielded a light amber liquid, and bulb-to-bulb distillation gave 19.82 g of 1-bromo-1-(nonafluorobutyl)undecane as a clear, colorless liquid, b.p. 120–170° C. at 0.06 torr (8 Pa).

A mixture of 15.03 g of 1-bromo-11-(nonafluorobutyl)undecane and 15.00 g of triethyl phosphite was heated at 150° C. After 18 hr, an additional 9.00 g of triethyl phosphite was added, and heating was continued for 24 hr. Diethyl ethylphosphonate and other volatiles were removed by distillation, b.p. 30–50° C. at 0.05 torr (7 Pa). Bulb-to-bulb distillation of the concentrate provided 16.07 g of 1-(diethylphosphono)-1-(nonafluorobutyl)undecane as a clear, colorless liquid, b.p. 170–200° C. at 0.05 torr (7 Pa).

To a solution of 15.23 g of 1-(diethylphosphono)-11-(nonafluorobutyl)undecane in 40 mL of dichloromethane was added 11.50 g of bromotrimethylsilane. After 24 hr at room temperature, the solution was concentrated to a pale yellowish liquid, and the intermediate silylphosphonate ester was dissolved in 200 mL of methanol. The resultant solution was stirred at room temperature for 30 min and concentrated to a white solid. Dissolution in methanol and concentration were repeated two times, and two recrystallizations of the crude product from heptane gave 10.85 g of 1-phosphono-11-(nonafluorobutyl)undecane $(CF_3(CF_2)_3(CH_2)_{11}PO_3H_2)$ as colorless plates, m.p. 93–96° C.

Example 3

The example describes the preparation of $CF_3(CF_2)_7(CH_2)_{11}PO_3H_2$.

To a solution of 41.10 g of perfluorooctyl iodide and 11.92 g of 10-undecen-1-ol in a mixture of 100 mL of acetonitrile and 40 mL of water was added a mixture of 6.89 g of sodium bicarbonate and 13.58 g of sodium dithionite in small portions with stirring. The reaction mixture was stirred at room temperature overnight and acidified with 1 N hydrochloric acid. The mixture was extracted with diethyl ether, and the combined organic phases were washed with saturated aqueous sodium bicarbonate and brine, and dried over anhydrous magnesium sulfate. Concentration afforded 43.2 g of crude 10-iodo-11-(heptadecafluorooctyl)-1-undecanol as a white solid, which was used without further purification.

To a slurry of 19.6 g of zinc powder in 150 mL of ethanol was added 4.0 g of acetic acid. A solution of the crude 10-iodo-11-(heptadecafluorooctyl)-1-undecanol prepared above in 50 mL of ethanol was added dropwise with stirring over 1 h, and the reaction mixture was heated at 50° C. for 4 hr. The mixture was filtered, the filtrate was concentrated to approximately 45 g of a soft, white solid, and this crude 11-(heptadecafluorooctyl)-1-undecanol was used without further purification.

To a mixture of 29.0 g of crude 11-(heptadecafluorooctyl)-1-undecanol and 250 mL of 48% hydrobromic acid was slowly added 25 mL of concentrated sulfuric acid. The reaction mixture was heated at 100° C. for 18 hr and poured into 1 liter of water. The mixture was extracted with hexanes, and the combined organic phases were washed with saturated aqueous sodium bicarbonate and dried over anhydrous magnesium sulfate. The solution was concentrated to a dark liquid, which was eluted through 3 inches of silica with hexanes. Concentration of the eluent afforded 20.2 g of crude 1-bromo-11-(heptadecafluorooctyl) undecane as a nearly white solid, which was used without further purification.

A mixture of 5.23 g of 1-bromo-11-(heptadecafluorooctyl)undecane and 4.2 g of triethyl phosphite was heated at 150° C. After 18 hr, diethyl ethylphosphonate and other volatiles were distilled from the reaction mixture, b.p. 30–50° C. at 0.05 torr (7 Pa). The concentrate was combined with an additional 2.0 g of triethyl phosphite, and the mixture was heated at 150° C. After 3 hr, volatiles were again distilled, and the crude 1-diethylphosphono-11-(heptadecafluorooctyl)undecane was dissolved in 10 mL of dichloromethane. To this solution was added 3.1 g of bromotrimethylsilane. After 18 hr at room temperature, the solution was concentrated to a nearly colorless liquid, and the intermediate silylphosphonate ester was dissolved in 200 mL of methanol. The resultant solution was stirred at room temperature for 3 hr and cooled to 0° C. The crude product was collected by filtration, and recrystallization from methanol afforded 2.32 g of 1-phosphono-11-(heptadecafluorooctyl)undecane $(CF_3(CF_2)_7(CH_2)_{11}PO_3H_2)$ as white crystals, m.p. 115–117° C.

Example 4

This example describes the preparation of $CF_3(CF_2)_3(CH_2)_{22}PO_3H_2$.

A solution of 5.08 g of 21-docosenoic acid in 50 mL of tetrahydrofuran was added dropwise with stirring to a slurry of 0.90 g of lithium aluminum hydride in 100 mL of tetrahydrofuran at 0° C., and the reaction mixture was stirred overnight at room temperature. Excess lithium aluminum hydride was quenched by the addition of 5 mL of ethyl acetate followed by 30 mL of 2 N aqueous sodium hydroxide. Lithium salts separated as a white, viscous mass, and the supernatant liquid was transferred to a separatory funnel. The precipitated salts were extracted with two 50 mL portions of diethyl ether, and the combined organic solutions were washed with 100 mL of water. The cloudy aqueous phase was acidified with 1 N aqueous hydrochloric acid and extracted with two 50 mL portions of diethyl ether. The combined organic phases were washed with brine and dried over anhydrous magnesium sulfate. Filtration and concentration provided 4.40 g of 21-docosen-1-ol as a white solid, m.p. 62–64° C., which was used without further purification.

A mixture of 4.00 g of 21-docosen-1-ol, 10.0 g of perfluorobutyl iodide, and 0.10 g of 2,2'-azobisisobutyronitrile was degassed and heated for 18 hr at 70° C. under a nitrogen atmosphere. The mixture was concentrated to give a light tan solid, which was dissolved in 20 mL of ethanol. This solution was added to a stirred slurry of 5.0 g of zinc powder in 50 mL of ethanol containing 10 drops of acetic acid. The mixture was heated at 50° C. for 3 hr and filtered. The filtrate was concentrated to give a white solid. Recrystallization of the crude product from heptane gave 6.96 g of an off-white solid. Further purification by column chromatography on silica, eluting with a 1:1 mixture of hexanes and diethyl ether, yielded 1.73 g of a white solid. The $^1$H NMR spectrum of the product indicated an approximately 9:1 mixture of 22-(nonafluorobutyl)-1-docosanol and 22-(nonafluorobutyl)-21-docosen-1-ol. The product was dissolved in a 1:1 mixture of hexanes and ethanol, 100 mg of 5 weight percent palladium on carbon was added, and this mixture was maintained at a pressure of 50 psi (350 kPa) of hydrogen on a Parr hydrogenator for 18 hr. Filtration and concentration left 1.69 g of 22-(nonafluorobutyl)-1-docosanol as a white solid, which was used without further purification.

To a mixture of 1.00 g of 22-(nonafluorobutyl)-1-docosanol and 30 mL of 48 weight percent hydrobromic acid was slowly added 3 mL of concentrated sulfuric acid, and the reaction mixture was heated at 100° C. for 24 hr. The mixture was cooled to room temperature, and the solid product was collected by filtration and dissolved in hexanes. The filtrate was extracted once with hexanes, and the combined hexanes solutions were washed with saturated aqueous sodium bicarbonate and brine, and dried over anhydrous magnesium sulfate. Filtration and concentration yielded 1.03 g of 1-bromo-22-(nonafluorobutyl)docosane as an off-white solid, which was used without further purification.

A mixture of 0.98 g of 1-bromo-22-(nonafluorobutyl) docosane and 4.00 g of triethyl phosphite was heated at 150° C. After 18 hr, diethyl ethylphosphonate and other volatiles were distilled, b.p. 30–50° C. at 0.05 torr (7 Pa), leaving 1.09 g of 1-(diethylphosphono)-22-(nonafluorobutyl)docosane as an off-white solid, which was used without further purification.

To a solution of 1.05 g of 1-(diethylphosphono)-22-(nonafluorobutyl)docosane in 10 mL of dichloromethane was added 0.61 g of bromotrimethylsilane. After 18 hr at room temperature, the solution was concentrated to a beige grease to which was added 30 mL of methanol. A white solid formed, and the resultant mixture was stirred at room temperature for 30 min. Removal of the solvent under reduced pressure left a white solid, which was slurried with an additional 20 mL of methanol for 30 min. Removal of solvent again left a white solid, and recrystallization of the crude product from methanol provided 0.61 g of 1-phosphono-22-(nonafluorobutyl)docosane ($CF_3(CF_2)_3$ $(CH_2)_{22}PO_3H_2$) as white crystals, m.p. 106–108° C.

Example 5

This example describes the preparation and evaluation of self-assembled films on a substrate.

Four-inch diameter silicon wafers coated with vacuum-deposited 500 nanometer thickness films of chromium, aluminum, copper, and nickel were obtained from WaferNet, San Jose, Calif. These were cut into quarters, and the pieces were subjected for 5 minutes to ultraviolet light and ozone in an apparatus in which an ultraviolet lamp (5 inch by 5 inch square (12.5 cm by 12.5 cm) ultraviolet lamp obtained under the trade designation "UV GRID LAMP" from BHK, Claremont, Calif., model 88-9102-02) was encased in a small sheet metal box (13 cm wide×14 cm deep×15 cm high) such that the lamp was suspended 8 cm above the bottom of the box. A small lab jack was used to position silicon wafer pieces to be cleaned as close as possible to the ultraviolet lamp without physically contacting the lamp. The front of the box was a door, hinged at the top, that allowed samples to be inserted and removed. A small hole in one side of the box was attached to a source of oxygen that flowed into the box at a rate of approximately 1 to 5 standard liters per minute.

Quarter-wafer pieces of ultraviolet light/ozone cleaned copper-, nickel-, and aluminum-coated silicon wafers were coated by immersion in a 0.1 weight percent solution of the indicated fluorinated phosphonic acid in denatured ethanol for 1 hr, followed by rinsing in fresh absolute ethanol and drying under a nitrogen stream. Static, advancing, and receding contact angles were measured for water and hexadecane on the metal-coated side of the coated wafer samples using a video contact angle analyzer having the trade designation "VCA-2500XE" obtained from AST Products, Billerica, Mass.

Quarter-wafer pieces of ultraviolet light/ozone cleaned chromium-coated silicon wafers were coated by spin coating (i.e., 5 sec at 300 revolutions per second, then 15 seconds at 2000 revolutions per minute) the wafer with a 0.1 weight percent solution of the indicated fluorinated phosphonic acid in denatured ethanol, heating the coated wafer at 150° C. for 3 min on a vacuum hotplate, then rinsing in fresh absolute ethanol, and drying under a nitrogen stream.

Water static angles were measured using 5 microliter drops, while advancing and receding angles were measured using 1–2 microliter drops. Reported contact angle measurements in Tables 1–4 (below) represent the average of measurements on opposite sides of at least three drops. Uncertainty in the contact angle measurements was estimated at +/−1 degree for static and advancing measurements, and +/−2 degrees for receding measurements. Deionized water (resistance≧18.2 megohm) and anhydrous hexadecane were used for contact angle measurements. Results are shown in Tables 1–4 (below).

Table 1 reports measured contact angles for water and hexadecane on chromium-coated silicon wafers.

TABLE 1

Contact Angles on Chromium-Coated Silicon Wafers

| Material | Water Static/Advancing/Receding (degrees/degrees/degrees) | Hexadecane Advancing/Receding (degrees/degrees) |
| --- | --- | --- |
| $CF_3(CF_2)_3(CH_2)_2PO_3H_2$ (Comparative) | 120/132/90 | 68/28 |
| $CF_3(CF_2)_7(CH_2)_2PO_3H_2$ (Comparative) | 126/137/101 | 81/43 |
| $CF_3(CF_2)_3(CH_2)_4PO_3H_2$ (Comparative) | 124/131/92 | 70/30 |
| $CF_3(CF_2)_3(CH_2)_6PO_3H_2$ (Comparative) | 128/135/95 | 78/34 |
| $CF_3(CF_2)_3(CH_2)_8PO_3H_2$ | 126/135/96 | 76/38 |
| $CF_3(CF_2)_3(CH_2)_{11}PO_3H_2$ | 132/139/99 | 81/41 |
| $CF_3(CF_2)_3(CH_2)_{22}PO_3H_2$ | 132/143/109 | 85/50 |
| $CF_3(CF_2)_7(CH_2)_{11}PO_3H_2$ | 135/143/112 | 90/54 |

Table 2 reports measured contact angles for water and hexadecane on aluminum-coated silicon wafers.

TABLE 2

Contact Angles on Aluminum-Coated Silicon Wafers

| Material | Water Static/Advancing/Receding (degrees/degrees/degrees) | Hexadecane Advancing/Receding (degrees/degrees) |
| --- | --- | --- |
| $CF_3(CF_2)_3(CH_2)_2PO_3H_2$ (Comparative) | 103/108/79 | 64/44 |
| $CF_3(CF_2)_7(CH_2)_2PO_3H_2$ (Comparative) | 114/119/108 | 75/58 |
| $CF_3(CF_2)_3(CH_2)_4PO_3H_2$ (Comparative) | 106/114/92 | 68/46 |
| $CF_3(CF_2)_3(CH_2)_6PO_3H_2$ (Comparative) | 110/116/100 | 69/52 |
| $CF_3(CF_2)_3(CH_2)_8PO_3H_2$ | 111/118/109 | 73/53 |
| $CF_3(CF_2)_3(CH_2)_{11}PO_3H_2$ | 114/120/110 | 73/56 |
| $CF_3(CF_2)_3(CH_2)_{22}PO_3H_2$ | 120/123/116 | 74/63 |
| $CF_3(CF_2)_7(CH_2)_{11}PO_3H_2$ | 122/125/118 | 80/70 |

Table 3 reports measured contact angles for water and hexadecane on copper-coated silicon wafers.

TABLE 3

Contact Angles on Copper-Coated Silicon Wafers

| Material | Water Static/Advancing/Receding (degrees/degrees/degrees) | Hexadecane Advancing/Receding (degrees/degrees) |
| --- | --- | --- |
| $CF_3(CF_2)_3(CH_2)_2PO_3H_2$ (Comparative) | 103/111/83 | 67/42 |
| $CF_3(CF_2)_7(CH_2)_2PO_3H_2$ (Comparative) | 115/119/106 | 76/54 |
| $CF_3(CF_2)_3(CH_2)_4PO_3H_2$ (Comparative) | 103/111/93 | 69/34 |
| $CF_3(CF_2)_3(CH_2)_6PO_3H_2$ (Comparative) | 104/114/93 | 71/37 |
| $CF_3(CF_2)_3(CH_2)_8PO_3H_2$ | 109/117/102 | 72/49 |
| $CF_3(CF_2)_3(CH_2)_{11}PO_3H_2$ | 112/116/100 | 73/53 |
| $CF_3(CF_2)_3(CH_2)_{22}PO_3H_2$ | 117/119/108 | 74/58 |
| $CF_3(CF_2)_7(CH_2)_{11}PO_3H_2$ | 115/121/105 | 79/64 |

Table 4 reports measured contact angles for water and hexadecane on nickel-coated silicon wafers.

TABLE 4

Contact Angles on Nickel-Coated Silicon Wafers

| Material | Water Static/Advancing/Receding (degrees/degrees/degrees) | Hexadecane Advancing/Receding (degrees/degrees) |
| --- | --- | --- |
| $CF_3(CF_2)_3(CH_2)_2PO_3H_2$ (Comparative) | 93/107/32 | 62/33 |
| $CF_3(CF_2)_7(CH_2)_2PO_3H_2$ (Comparative) | 118/131/95 | 78/55 |
| $CF_3(CF_2)_3(CH_2)_4PO_3H_2$ (Comparative) | 106/120/64 | 68/40 |
| $CF_3(CF_2)_3(CH_2)_6PO_3H_2$ (Comparative) | 111/125/81 | 71/44 |
| $CF_3(CF_2)_3(CH_2)_8PO_3H_2$ | 115/128/100 | 76/49 |
| $CF_3(CF_2)_3(CH_2)_{11}PO_3H_2$ | 117/130/102 | 75/50 |
| $CF_3(CF_2)_3(CH_2)_{22}PO_3H_2$ | 123/135/110 | 78/50 |
| $CF_3(CF_2)_7(CH_2)_{11}PO_3H_2$ | 126/136/111 | 85/57 |

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A fluorinated phosphonic acid compound having the formula:

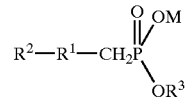

wherein:

$R^1$ is a straight chain alkylene group having from about 7 to about 21 carbon atoms;

$R^2$ is a perfluoro-n-butyl group;

$R^3$ is hydrogen, an alkali metal cation, or an alkyl group having from about 1 to about 6 carbon atoms; and M is hydrogen or an alkali metal cation.

2. The compound of claim 1, wherein at least one of $R^3$ or M is hydrogen.

3. The compound of claim 1, wherein $R^1$ is a straight chain alkylene group having front about 10 to about 21 carbon atoms.

4. The compound of claim 1, wherein $R^1$ is decane-1,10-diyl or heneicosane-1,21-diyl.

5. The compound of claim 1, wherein $R^1$ is decane-1,10-diyl.

6. The compound of claim 1, wherein the compound is selected from the group consisting of $CF_3(CF_2)_3(CH_2)_8PO_3H_2$, $CF_3(CF_2)_3(CH_2)_{11}PO_3H_2$, $CF_3(CF_2)_3(CH_2)_{22}PO_3H_2$.

7. A method of treating the surface of an article, the method comprising:

providing a substrate having a surface; and applying a fluorinated phosphonic acid compound to the surface of the substrate, the compound having the formula:

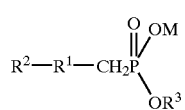

wherein:
$R^1$ is a straight chain alkylene group having from about 7 to about 21 carbon atoms;
$R^2$ is a perfluoro-n-butyl group;
$R^3$ is hydrogen, an alkali metal cation, or an alkyl group having from about 1 to about 6 carbon atoms; and
M is hydrogen or an alkali metal cation.

8. The method of claim 7, wherein at least one of $R^3$ or M is hydrogen.

9. The method of claim 7, wherein $R^1$ is a straight chain alkylene group having from about 10 to about 21 carbon atoms.

10. The method of claim 7, wherein $R^1$ is decane-1,10-diyl or heneicosane-1,21-diyl.

11. The method of claim 7, wherein the substrate comprises metal.

12. The method of claim 11, wherein the metal is selected from the group consisting of aluminum, nickel, chromium, copper, and silver.

13. The method of claim 7, wherein the compound is selected from the group consisting of $CF_3(CF_2)_3(CH_2)_8PO_3H_2$, $CF_3(CF_2)_3(CH_2)_{11}PO_3H_2$, $CF_3(CF_2)_3(CH_2)_{22}PO_3H_2$.

14. An article comprising a substrate having a surface, the surface intimately contacting at least a partial monolayer of a fluorinated phosphonic acid compound having the formula:

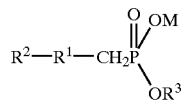

wherein:
$K^1$ is a straight chain alkylene group having from about 7 to about 21 carbon atoms;
$R^2$ is a perfluoro-n-butyl group;
$R^3$ is hydrogen, an alkali metal cation, or an alkyl group having from about 1 to about 6 carbon atoms; and
M is hydrogen or an alkali metal cation.

15. The article of claim 14, wherein at least one of $R^3$ or M is hydrogen.

16. The article of claim 14, wherein $R^1$ is a straight chain alkylene group having from about 10 to about 21 carbon atoms.

17. The article of claim 15, wherein $R^1$ is decane-1,10-diyl or heneicosane-1,21-diyl.

18. The article of claim 14, wherein the substrate comprises metal.

19. The article of claim 18, wherein the metal is selected from the group consisting of aluminum, nickel, chromium, copper, and silver.

20. The article of claim 14, wherein the compound is selected from the group consisting of $CF_3(CF_2)_3(CH_2)_8PO_3H_2$, $CF_3$, $(CF_2)_3(CH_2)_{11}PO_3H_2$, $CF_3(CF_2)_3(CH_2)_{22}PO_3H_2$.

21. An article prepared by a process, the process comprising:
providing a substrate having a surface; and
applying a fluorinated phosphonic acid compound to the surface of the substrate, the
compound having the formula:

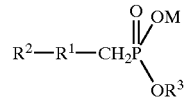

wherein:
$R^1$ is a straight chain alkylene group having from about 7 to about 21 carbon atoms;
$R^2$ is a perfluoro-n-butyl group;
$R^3$ is hydrogen, an alkali metal cation, or an alkyl group having from about 1 to about 6 carbon atoms; and
M is hydrogen or an alkali metal cation.

22. The article of claim 16, wherein the compound is selected from the group consisting of $CF_3(CF_2)_3(CH_2)_8PO_3H_2$, $CF_3(CF_2)_3(CH_2)_{11}PO_3H_2$, $CF_3(CF_2)_3(CH_2)_{22}PO_3H_2$.

* * * * *

UNITED STATES PATENT AND TRADEMARK OFFICE
CERTIFICATE OF CORRECTION

PATENT NO. : 6,824,882 B2
DATED : November 30, 2004
INVENTOR(S) : Boardman, Larry D.

It is certified that error appears in the above-identified patent and that said Letters Patent is hereby corrected as shown below:

Title page,
Item [75], Inventors, insert -- Naiyong Jing, Woodbury, MN (US) -- following "Mark J. Pellerite, Woodbury, MN (US)".

Column 9,
Line 47, delete "1" following "bromo-" and insert -- 11 -- in place thereof.
Line 56, delete "1" following "(diethylphosphono)" and insert -- 11 -- in place thereof.

Column 14,
Line 50, delete "front" and insert -- from -- in place thereof.
Line 60, insert -- , and $CF_3(CF_2)_7(CH_2)_{11}PO_3H_2$ -- following "$PO_3H_2$".

Column 15,
Line 30, insert -- , and $CF_3(CF_2)_7(CH_2)_{11}PO_3H_2$ -- following "$PO_3H_2$".
Line 42, delete "$K^1$" and insert -- $R^1$ -- in place thereof.

Column 16,
Line 9, delete "15" and insert -- 14 -- in place thereof.
Line 18, delete "," following -- CF3 --.
Lines 19 and 43, insert -- , and $CF_3(CF_2)_7(CH_2)_{11}PO_3H_2$ -- following "$PO_3H_2$".
Line 34, delete "group" following "n-butyl".

Signed and Sealed this

Sixteenth Day of August, 2005

JON W. DUDAS
*Director of the United States Patent and Trademark Office*